United States Patent [19]

Malawer et al.

[11] Patent Number: 5,458,871

[45] Date of Patent: Oct. 17, 1995

[54] 0% VOC, SINGLE PHASE HAIR SPRAY COMPOSITION

[75] Inventors: Edward G. Malawer, Wayne; Kolazi S. Narayanan, Palisades Park, both of N.J.; James Cullen, Bartonsville, Pa.; Colleen M. Rocafort, Lake Hiawatha, N.J.

[73] Assignee: ISP Investments Inc., Wilmington, Del.

[21] Appl. No.: 294,464

[22] Filed: Aug. 23, 1994

[51] Int. Cl.$^6$ ................... A61K 7/11; A61K 7/06
[52] U.S. Cl. ................... 424/47; 424/43; 424/45; 424/70.1; 424/70.11; 424/70.31; 424/401; 424/DIG. 1; 424/DIG. 2
[58] Field of Search ................... 424/45, 47, 43, 424/DIG. 1, DIG. 2, 401, 70, 71, 70.1, 70.11, 70.31

[56] References Cited

U.S. PATENT DOCUMENTS

| | | | |
|---|---|---|---|
| 4,164,562 | 8/1979 | Nandagiri | 424/47 |
| 4,733,677 | 3/1988 | Gee | 132/7 |
| 4,985,239 | 1/1991 | Yahagi | 424/70 |
| 5,068,315 | 11/1991 | Buultjens | 530/324 |
| 5,077,040 | 12/1991 | Bergmann | 424/70 |
| 5,225,190 | 7/1993 | Halloran | 424/70 |

Primary Examiner—Gollamudi S. Kishore
Attorney, Agent, or Firm—Walter Katz; Marilyn J. Maue; Joshua J. Ward

[57] ABSTRACT

A 0% VOC, single phase hair spray composition of a water-insoluble polymer wherein substantially all the particles therein have a diameter of less than 1 micron, i.e. a microemulsion.

6 Claims, No Drawings

0% VOC, SINGLE PHASE HAIR SPRAY COMPOSITION

BACKGROUND OF THE INVENTION

1. Field of the Invention

This invention relates to hair spray compositions, and, more particularly, to a 0% VOC, single phase hair spray composition of a water-insoluble polymer wherein substantially all particles therein have a diameter of less than 1 micron, i.e. a microemulsion.

2. Description of the Prior Art

Hair spray compositions generally are solutions of a hair fixative polymer and a solvent, usually ethanol, water or ethanol-water mixtures, as described in U.S. Pat. Nos. 4,543,249; 4,798,721; 4,923,694; 4,985,239; 5,266,308; 5,085,859; 5,173,290; 5,176,898; and PCT WO 93/03705. Such compositions also may contain small quantities of one or more adjuvants normally found in cosmetic products including a small quantity of a surfactant. The presence of a surfactant in a hair spray composition reduces the surface tension between the aqueous and polymer phases in the composition, and provides sprays having a desirable small droplet size or mist. U.S. Pat. Nos. 4,543,249 and 5,176,898, for example, describe such a surfactant-containing system for water-soluble fixative polymers. Similarly, U.S. Pat. No. 5,085,859 discloses a hair treating composition containing a film-forming material which is an interpenetrating polymer network of a substituted vinyl copolymer having a polar functionality and a non-polar silsesquioxane. This patent suggests that the interpenetrating polymer might be incorporated into the composition as an emulsion or microemulsion; however, such formulations are not disclosed for an interpenetrating polymer, or for any other polymer.

Water-insoluble polymers, such as the ethyl and butyl half-esters of copolymers of maleic anhydride and methyl vinyl ether, known as GANTREZ®-ES resins, and sold by International Specialty Products (Wayne, N.J.), have been used for many years as the hair fixative resin of choice in alcohol-based hair spray compositions, both in non-aerosol (pump) and aerosol (propellant) delivery systems. Recent California state legislation, however, has required that future commercial hair spray compositions contain a low volatile organic compound (VOC) content therein, particularly 80% or less VOC (by 1994) and 55% or less VOC (by 1998). In order to meet these strict VOC standards, it has been necessary for hair spray formulators to substantially reduce the alcohol content and to substantially increase the water content of existing hair spray products. However, for water-insoluble polymers, such as GANTREZ®-ES resins, which do not dissolve readily in water-based systems, such changes produce two-phase systems, which is undesirable from a commercial standpoint.

Accordingly, it is an object of the present invention to provide a 0% VOC hair spray composition containing a water-insoluble polymer in the form of a single phase system.

Another object of the invention is to provide a 0% VOC, single phase hair spray composition which includes a water-insoluble polymer, a surfactant and water, and in which substantially all the particles therein have a diameter of less than 1 micron.

Still another object of the present invention is the provision of a clear, single phase, pumpable or propellant-actuated, 0% VOC hair spray composition including the ethyl half-ester of a copolymer of maleic anhydride and methyl vinyl ether as the hair fixative, a surfactant and water, and, optionally, a non-VOC cosolvent.

A particular object of the invention is to provide a clear, single phase, 0% VOC hair spray composition of a water-insoluble fixative resin in the form of a microemulsion.

These and other objects and features of the invention will be made apparent from the following more particular description of the invention.

SUMMARY OF THE INVENTION

A 0% VOC hair spray composition is provided herein which is a single phase system of a water-insoluble polymer in which substantially all the particles therein have a diameter of less than 1 micron, i.e. a microemulsion, preferably 0.1 micron or less, and optimally 0.05 micron or less, which comprises, by weight of the composition:

(a) a water-insoluble polymer, preferably the ethyl half-ester of a copolymer of maleic anhydride and methyl vinyl ether, in an amount of 0.5–10%, preferably 2–5%, optionally neutralized up to 33 mole %, preferably 5–24 mole % of the polymer;

(b) a surfactant, preferably a polyethoxylated glycol ether of glyceryl isostearate or monoleate, in an amount of 0.2–15%, preferably 2–10%;

(c) water to 100%, preferably 75–90%, and optionally, (d) a non-VOC cosolvent, preferably selected from among N-methylpyrrolidone (NMP), propylene glycol, polyethylene glycol (PEG), butyrolactone, propylene carbonate and the like, in an amount of 0–20%, preferably 0–10

The 0% VOC, single phase hair spray compositions of the invention can be applied in a pump or propellant spray delivery system, preferably a pump system, as a fine spray having a good spray pattern. The fixative film thus-formed on the hair of the user exhibits the desirable performance characteristics of a water-based hair spray system of good hold and acceptable high humidity curl retention, drying times and tack.

DETAILED DESCRIPTION OF THE INVENTION

In the present invention, solubilization of a water-insoluble polymer, such as the ethyl half-ester of a copolymer of maleic anhydride and ethyl vinyl ether, into a 0% VOC hair spray composition which is a single-phase system with particles having a size of less than 1 micron in diameter, i.e. a microemulsion, is accomplished herein by predetermining (1) the kind and amount of water-insoluble resin, (2) the kind and amount of surfactant, (3) the extent of neutralization of the water-insoluble polymer, and (4) the presence or absence of a non-VOC cosolvent.

(a) Water-Insoluble Polymer

Suitable water-insoluble polymers for use herein include alkyl half-esters of copolymers of maleic anhydride and an alkyl vinyl ether. Such polymers have the general formula:

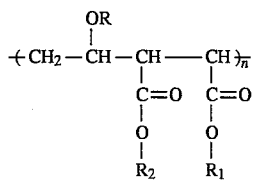

where

R=$C_1$–$C_{18}$ alkyl, preferably methyl, $R_1$=$R_2$=H or $C_1$–$C_{18}$ alkyl, preferably ethyl, at least one of $R_1$ or $R_2$=H, and n=50–1000, preferably 100.

One such polymer is GANTREZ® ES-225, which is available commercially as a 50% solution of the resin in ethanol. The resin in solid form is preferred for preparing the 0% VOC hair spray composition of the invention, and it may be obtained simply by removing the ethanol from the commercial solution, as for example, by distillation or spray-drying.

Suitably, the water-insoluble resin is present in an amount of 0.5–10%, preferably 1–5%, by weight of the composition.

(a-1) Neutralization of Water-Insoluble Polymer

Suitable neutralizing agents include aminomethylpropanol (AMP), tertiary-isopropanolamine (TIPA), dimethylstearylamine, dodecylamine and triethanolamine.

The water-insoluble polymer may be neutralized, if desired, to an extent of up to 33 mole %, preferably 5–50 mole %, of the polymer.

(b) Surfactant

Suitable surfactants for use herein include ethoxylated glyceryl fatty acid esters, suitably with an HLB of >10, preferably about 12–18, and optimally about 14–16, and containing about 5–50 ethylene oxide (EO) units, preferably 15–35, and optimally about 20–30.

The alkyl group of the fatty acid ester suitably includes about 10–18 carbon atoms, saturated or unsaturated, e.g. stearyl, isostearyl, oleyl, etc. Taget® I (PEG-30 glyceryl isostearate) (Goldschmidt) or Taget® 02 (polyoxyethylene glycerol monooleate) surfactant compounds are preferred. Other suitable surfactants include ethoxylated natural wool fat, e.g. Ethoxylan® 1686 (PEG 75 lanolin); and a quaternized lanolin such as Lanoquat® 1751A.

Mixtures of surfactants also may be used herein. Accordingly, the compound cocoamidopropyl betaine (Velvetex® Blc 35) may be used as a cosurfactant.

The surfactant is present in an amount of 0.2–15%, preferably 2–10%, by weight of the composition.

(c) Water

Water is present to 100% by weight of the composition, preferably 75–90%.

(d) Optional Non-VOC Cosolvent

At relatively high polymer concentrations, for example, 5–10%, it may be desirable to include a cosolvent in the composition. Suitable cosolvents are themselves non-VOC materials, such as N-methylpyrrolidone (NMP), propylene glycol, polyethylene glycol (PEG), butyrolactone, propylene carbonate, and the like, generally in an amount of 0–20%, preferably 0–15%, by weight of the composition.

EXAMPLES

The hair spray compositions of the invention exhibit those physical characteristics indicative of a microemulsion, that is, a clear, single phase system in which substantially all the particles therein have a diameter of less than 1 micron, preferably less than 0.1 micron, and, optimally, less than 0.05 micron.

Some compositions may appear hazy, particularly at high polymer concentrations; however, this effect probably is caused by trace amounts of other materials present in the commercial polymer rather than to an intrinsic change in the microemulsion itself. The inclusion of a cosolvent in the formulation will clear up the composition.

The 0% VOC, single phase hair spray compositions of the invention can be applied by a pump or propellant spray delivery system, preferably a pump system, as a coarse spray having a good spray pattern. The fixative film thus-formed on the hair of the user exhibits the desirable performance characteristics of a water-based hair spray system of good hold and acceptable high humidity curl retention, drying times and tack.

Working examples of the invention and their performance during use are given in Table 1 below. The results were obtained using a Seaquist Euromist II pump spray system capable of delivering a 140–160 µl output from an actuator of 0.018"×0.010" deep. The pH of the compositions was 4.89–4.97.

TABLE 1

| Comp. No. | Wt. Gantrez® ES-225 (as solid) | Surfactant | Wt. of Surfactant | Cosolvent | Wt. Cosolvent | Wt. Water | Neutralizing Agent | Wt. Neutralizing Agent | Appearance of Composition |
|---|---|---|---|---|---|---|---|---|---|
| 1 | 2.0 | Taget I | 10 | — | — | 88.00 | — | — | Clear* |
| 2 | 2.0 | Taget I | 10 | — | — | 87.81 | TIPA | 0.19 | Clear |
| 3 (Control) | 2.0 | — | — | — | — | 98.00 | — | — | Insoluble; solid separates |
| 4 (Control) | 2.0 | — | — | — | — | 97.81 | TIPA | 0.19 | Insoluble; solid separates |
| 5 | 5.0 | Taget I | 10 | — | — | 84.78 | AMP | 0.22 | Soluble system; hazy |
| 6** | 5.0 | Taget I | 10 | NMP | 10 | 74.78 | AMP | 0.22 | Clear |
| 6A | 5.0 | Taget I | 10 | — | — | 84.78 | AMP | 0.22 | Cloudy, no solid |
| 6B | 5.0 | Taget I | 10 | — | — | 85.00 | — | — | Insoluble; cloudy |
| 6C | 5.0 | Taget I | 10 | NMP | 5 | 80.00 | — | — | Insoluble, cloudy |

TABLE 1-continued

| Comp. No. | Wt. Gantrez® ES-225 (as solid) | Surfactant | Wt. of Surfactant | Cosolvent | Wt. Cosolvent | Wt. Water | Neutralizing Agent | Wt. Neutralizing Agent | Appearance of Composition |
|---|---|---|---|---|---|---|---|---|---|
| 6D | 5.0 | Taget I | 10 | NMP | 5 | 79.78 | AMP | 0.22 | Soluble, slightly cloudy |
| 6E | 5.0 | Taget I | 8 | — | — | 86.78 | AMP | 0.22 | Soluble, turbid |
| 6F | 5.0 | Taget I | 6 | — | — | 88.78 | AMP | 0.22 | Soluble, turbid |
| 6G | 5.0 | Taget I | 4 | — | — | 90.78 | AMP | 0.22 | Soluble, turbid |
| 6H | 5.0 | Taget I | 2 | — | — | 92.78 | AMP | 0.22 | Soluble, turbid |
| 6I | 5.0 | Taget I | — | — | — | 94.78 | AMP | 0.22 | Insoluble, cloudy |
| 7 | 5.0 | Taget I | 8 | — | — | 86.78 | AMP | 0.22 | Soluble system; hazy |
| 8 | 5.0 | Taget I | 2 | — | — | 92.78 | AMP | 0.22 | Soluble system; hazy |
| 8A*** | 5.0 | Taget I | — | — | — | 94.78 | AMP | 0.22 | Insoluble |
| 9 | 2.0 | Taget I | 10 | PEG | 4.5 | 83.50 | AMP | 0.22 | Clear pH 4.89; particle size 0.01µ–0.02µ |

*Clear = optically transparent and free of haze.
**Shows the effect of presence of cosolvent in formulations 5 and 6.
***Comparative example.

The examples in Table 1 demonstrate that water solubilization of hair resins is a function of (a) degree of neutralization of the resin, (b) the chemical structure of the surfactant used, (c) the amount of surfactant and, particularly, (d) the nature and amount of cosolvent.

Table 2 below shows the advantageous performance characteristics of the hair spray compositions of the invention during use under standard test conditions. The results are shown for representative hair spray composition Example 8 of Table 1.

TABLE 2

| Performance of Hair Spray Composition of Invention Composition No. | |
|---|---|
| Characteristic | |
| Film clarity | Clear |
| Film hardness | >9B |
| Lond term hold 90 min (%) | 58.95% |
| Dry time (sec.) | 117 |
| Duration of tack (sec.) | 72 |
| Stiffness | 5.0 |
| Non-flaking | 8.0 |
| Combability | 9.0 |
| Removability | Acceptable |
| Pump spray droplet particle size (µ) | 109.74µ |
| Pump spray pattern (in.) | 3½ |
| Pump spray pattern | Coarse |

While the invention has been described with particular reference to certain embodiments thereof, it will be understood that changes and modifications may be made which are within the skill of the art. Accordingly, it is intended to be bound only by the following claims, in which:

What is claimed is:

1. A 0% volatile organic compound, single phase hair spray composition in which substantially all the particles therein have a diameter of less than 1 micron, comprising, by weight of the composition, (a) a polymer which is the half-ester of a copolymer of maleic anhydride and methyl vinyl ether in an amount of 0.5%–10%, optionally neutralized up to 33 mole % of the polymer, (b) a surfactant which is a polyethoxylated glycol ether of glyceryl isostearate or monoleate having an HLB of greater than 10, in an amount of 0.2–10%, and (c) water to 100%, and, optionally (d) a non-volatile organic compound cosolvent which is propylene glycol to solubilize said polymer when present in higher amounts of said range in an amount of 0–20%.

2. A 0% volatile organic compound, single phase hair spray composition according to claim 1 wherein (a) is 2–5%, and 5–20 mole %, (b) is 2–10%, (c) is 75–90%, and (d) is 0–15%.

3. A 0% volatile organic compound, single phase hair spray composition according to claim 1 wherein the particle size is 0.1 micron or less.

4. A composition according to claim 1 which is a microemulsion.

5. A composition according to claim 1 wherein (b) has an HLB of 12–18.

6. A composition according to claim 1 wherein (a) is 5–10%, and (d) is present in an amount of up to 10%.

* * * * *